United States Patent
Barzaghi et al.

(10) Patent No.: US 7,115,780 B2
(45) Date of Patent: Oct. 3, 2006

(54) PROPANOLAMINOMETHYLTETRALINES, THEIR PREPARATION AND PHARMACEUTICAL COMPOSITION COMPRISING SAME

(75) Inventors: Laura Barzaghi, Monza (IT); Roberto Cecchi, Lodi (IT); Nunzia Viviani, Cantu (IT)

(73) Assignee: Sanofi-Aventis, Paris (FR)

( * ) Notice: Subject to any disclaimer, the term of this patent is extended or adjusted under 35 U.S.C. 154(b) by 45 days.

(21) Appl. No.: 10/497,379

(22) PCT Filed: Dec. 2, 2002

(86) PCT No.: PCT/FR02/04129

§ 371 (c)(1),
(2), (4) Date: Jun. 2, 2004

(87) PCT Pub. No.: WO03/048117

PCT Pub. Date: Jun. 12, 2003

(65) Prior Publication Data

US 2005/0054641 A1    Mar. 10, 2005

(30) Foreign Application Priority Data

Dec. 5, 2001  (FR)  ................................. 01 15684

(51) Int. Cl.
- *C07C 211/19* (2006.01)
- *C07C 213/02* (2006.01)
- *C07C 307/02* (2006.01)
- *C07D 263/52* (2006.01)
- *C07D 265/36* (2006.01)
- *A61K 31/18* (2006.01)
- *A61K 31/42* (2006.01)

(52) U.S. Cl. .................. 564/308; 564/99; 564/399; 548/217; 544/105; 514/230.5; 514/375; 514/605; 514/647

(58) Field of Classification Search ............. None
See application file for complete search history.

(56) References Cited

U.S. PATENT DOCUMENTS

| | | | |
|---|---|---|---|
| 4,004,028 A | | 1/1977 | Kaiser |
| 5,194,450 A | * | 3/1993 | McDermed et al. ........ 514/605 |
| 5,254,595 A | | 10/1993 | Guzzi et al. |
| 2004/0034070 A1 | * | 2/2004 | Barzaghi et al. ............ 514/357 |

FOREIGN PATENT DOCUMENTS

| | | |
|---|---|---|
| EP | 0 375 560 A1 | 12/1989 |
| WO | WO 99 51564 | 10/1999 |

* cited by examiner

Primary Examiner—Brian Davis
(74) Attorney, Agent, or Firm—Jiang Lin; Paul DuPont

(57) ABSTRACT

The invention concerns compounds of formula (I), wherein A is a group of formula (a) or (b), wherein: R represents a hydrogen or halogen atom, a —S(O)$_z$(C$_1$–C$_4$)Alk wherein z is 0, 1 or 2, a —NHSO$_2$(C$_1$–C$_4$)Alk, —SO$_2$NH(C$_1$–C$_4$)Alk, —NHSO$_2$—(C$_1$–C$_4$)Alk-phenyl or —NHSO$_2$-phenyl group, said phenyl capable of bearing a halogen atom, a (C$_1$–C$_4$)Alk group or a (C$_1$–C$_6$)alkoxy group; R$_1$ represents a hydrogen atom or a —(C$_1$–C$_4$)Alk, —CO(C$_1$–C$_4$)Alk, —(C$_1$–C$_4$)Alk-phenyl or —CO-phenyl group, said phenyl capable of bearing a halogen atom or a —(C$_1$–C$_4$)Alk or (C$_1$–C$_6$)alkoxy group; R$_2$ is a hydrogen atom, a —SO$_2$(C$_1$–C$_4$)Alk, —SO$_2$—(C$_1$–C$_4$)Alk-phenyl, —SO$_2$-phenyl group, or a —(C$_1$–C$_4$)Alk group; X completes a saturated or unsaturated cycle of 5 to 8 atoms, capable of bearing one or two —(C$_1$–C$_4$)Alk groups and/or two carbonyl groups; R$_3$ and R'$_3$ represent each independently a hydrogen or halogen atom, a —(C$_1$–C$_6$)Alk, hydroxy, —CN, —(C$_1$–C$_6$)alkoxy, —COR$_4$ or Y—CR$_8$R$_9$—COR$_4$ group; Y represents O or CH$_2$; R$_4$ represents a hydroxy, (C$_1$–C$_6$)alkoxy or —NR$_5$R$_6$ group; R$_5$ and R$_6$ independently represent a hydrogen atom, a —(C$_1$–C$_4$)Alk, group, aryl or heteroaryl optionally substituted by a R$_7$ group, aralkyl or heteroaralkyl optionally substituted by a R$_7$ group; or R$_5$ and R$_6$, with the nitrogen atom which bears them, form a saturated or unsaturated cycle of 5 to 7 atoms optionally substituted by a R$_7$ group; and R$_7$ represents a hydrogen or halogen atom, a hydroxy, —(C$_1$–C$_4$)Alk, —(C$_1$–C$_6$)alkoxy, —NH(C$_1$–C$_4$)Alk, —N(C$_1$–C$_4$)Alk$_2$, —COO(C$_1$–C$_4$)Alk, aralkyl or heteroaryl group; R$_8$ and R$_9$ independently represent a hydrogen atom or a —(C$_1$–C$_4$)Alk group; their salts or solvates, the pharmaceutical compositions containing them, a method for preparing them and synthesis intermediates

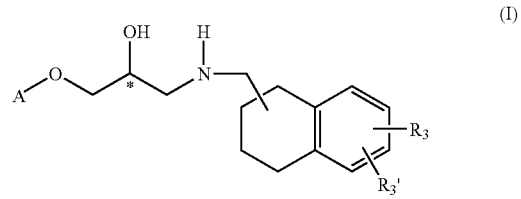

(I)

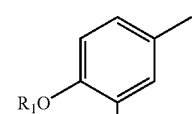

(a)

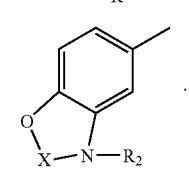

(b)

23 Claims, No Drawings

PROPANOLAMINOMETHYLTETRALINES, THEIR PREPARATION AND PHARMACEUTICAL COMPOSITION COMPRISING SAME

The present invention relates to novel phenoxypropanolamines, to pharmaceutical compositions containing them, to a process for their preparation and to intermediates in said process.

WO-A-99/51564 describes propanolamine derivatives having an agonist activity as regards beta-3 adrenergic receptors and being capable of being used in treating a number of disorders such as ulcers, pancreatitis, obesity, urinary incontinence and pollakiuria.

EP-A-0 375 560 describes aryloxypropanol-aminotetralins that also have an activity as regards beta-3 adrenergic receptors but exercise an antagonist effect on these receptors.

It has now been discovered that certain phenoxypropanolaminotetralins with a structure close to that of compounds described in EP-A-0 375 560 have an agonist activity as regards beta-3 adrenergic receptors.

In one aspect, the present invention thus concerns phenoxypropanolamines of general formula (I):

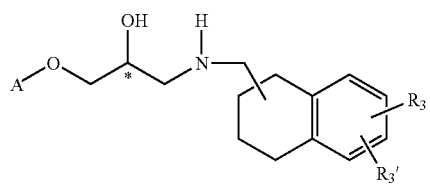

(I)

in which:

A is a group of formula (a) or (b)

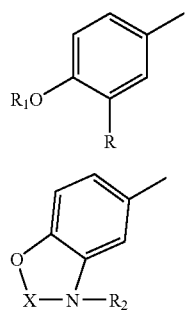

where

R represents a hydrogen or halogen atom, an —S(O)$_2$(C$_1$–C$_4$)alk group where z is 0, 1 or 2, an —NHSO$_2$(C$_1$–C$_4$)alk, —SO$_2$NH(C$_1$–C$_4$)alk, —NHSO$_2$—(C$_1$–C$_4$)alk-phenyl or —NHSO$_2$-phenyl group, it being possible for said phenyl to carry a halogen atom, a (C$_1$–C$_4$)alk group or a (C$_1$–C$_6$)alkoxy group;

R$_1$ represents a hydrogen atom or a —(C$_1$–C$_4$)alk, —CO(C$_1$–C$_4$)alk, —(C$_1$–C$_4$)alk-phenyl or —CO-phenyl group, it being possible for said phenyl to carry a halogen atom or a —(C$_1$–C$_4$)alk or (C$_1$–C$_6$)alkoxy group;

R$_2$ is a hydrogen atom, an —SO$_2$(C$_1$–C$_4$)alk, —SO$_2$—(C$_1$–C$_4$)alk-phenyl, —SO$_2$-phenyl, or a —(C$_1$–C$_4$)alk group;

X completes a saturated or unsaturated 5- to 8-atom ring which can carry one or two —(C$_1$–C$_4$)alk groups and/or one or two carbonyl groups;

R$_3$ and R'$_3$ each represent independently a hydrogen or halogen atom, a —(C$_1$–C$_6$)alk, hydroxyl, —CN, —(C$_1$–C$_6$)alkoxy, —COR$_4$ or —Y—CR$_8$R$_9$—COR$_4$ group;

Y represents O or CH$_2$;

R$_4$ represents a hydroxyl, (C$_1$–C$_6$)alkoxy or —NR$_5$R$_6$ group;

R$_5$ and R$_6$ represent independently a hydrogen atom; a —(C$_1$–C$_4$)alk, aryl or heteroaryl group optionally substituted with an R$_7$ group, an aralkyl or heteroaralkyl group optionally substituted with an R$_7$ group;

or else R$_5$ and R$_6$, with the nitrogen atom carrying them, form a saturated or unsaturated 5- to 7-atom ring optionally substituted with an R$_7$ group; and R$_7$ represents a hydrogen or halogen atom, a hydroxyl, —(C$_1$–C$_4$)alk, —(C$_1$–C$_6$)alkoxy, —NH(C$_1$–C$_4$)alk, —N(C$_1$–C$_4$)alk$_2$, —COO(C$_1$–C$_4$)alk, aralkyl or heteroaralkyl group;

R$_8$ and R$_9$ represent independently a hydrogen atom or a —(C$_1$–C$_4$)alk group;

and their salts or solvates.

In the present description, the terms "—(C$_1$–C$_4$)alk" and "—(C$_1$–C$_6$)alk" designate monovalent radicals of a hydrocarbon having a saturated linear or branched chain.

In the present description, the term "—(C$_1$–C$_6$)alkoxy" designates a monovalent radical of a saturated straight, branched or cyclic chain hydrocarbon, attached to the remainder of the molecule by an oxygen atom.

Preferred aryl or heteroaryl groups include in particular phenyl, naphthyl and pyridyl.

The aralkyl or heteroalkyl groups respectively designate arylalkyl or heteroarylalkyl groups attached to the remainder of the molecule by the alkyl chain.

Preferred aralkyl or heteroaralkyl groups include in particular benzyl, naphthylmethyl and pyridylmethyl.

The saturated or unsaturated 5- to 7-atom rings include in particular pyrrolidine, piperidine, morpholine and thiomorpholine.

Preferred compounds are those where A is a group of formula (a).

Other preferred compounds are those where R is an —NHSO$_2$(C$_1$–C$_4$)alk group.

Other preferred compounds are those where R$_1$ is a hydrogen atom.

Other preferred compounds are those where R$_3$ and/or R$_{13}$ are a hydrogen atom, a hydroxyl, (C$_1$–C$_6$)alkoxy or —Y—CR$_8$R$_9$—COOCH$_2$—CH$_3$ group.

Salts of the compounds of formula (I) in accordance with the present invention include addition salts with pharmaceutically acceptable mineral or organic acids such as the hydrochloride, hydrobromide, sulfate, bisulfate, dihydrogenphosphate, citrate, maleate, tartrate, fumarate, gluconate, methanesulfonate, 2-naphthalenesulfonate, etc., as well as addition salts that enable appropriate separation or crystallization of the compounds of formula (I), such as the picrate or oxalate, or addition salts with optically active acids, for example camphosulfonic acids and mandelic acids or substituted mandelic acids.

Further, when the compounds of formula (I) contain a free carboxy group, the salts also include salts of mineral bases, preferably those with alkali metals such as sodium or potassium, or of organic bases.

The tetralin may be attached to the aminomethyl group by the carbon at the alpha- or beta-position, the carbon for attachment of the tetralin being an asymmetric carbon.

Optically pure stereoisomers and mixtures of isomers of the compounds of formula (I) due to asymmetric carbon atoms in any proportion are also encompassed by the present invention.

Preferred compounds of formula (I) are compounds in which the configuration of the carbon carrying the OH group in the propanolamine is (S).

The compounds of formula (I) can be prepared by treating a compound of formula (II):

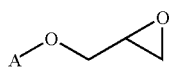
(II)

in which A is as indicated above, with an amine of formula (III):

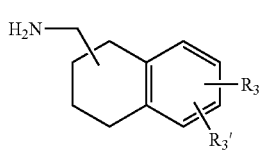
(III)

in the form of a nonsalified base, where $R_3$ and $R'_3$ are as defined above, and optionally by converting the compound of formula (I) thus obtained into one of its salts.

More particularly, the reaction between the compounds of formula (II) and (III) is carried out in an organic solvent such as a lower alcohol, for example: methanol, ethanol or propan-2-ol; dimethylsulfoxide (DMSO); a linear or cyclic ether; or an amide such as dimethylformamide (DMF) or dimethylacetamide; preferably using at least equimolecular quantities of reactants.

The reaction temperature is in the range from ambient temperature to the reflux temperature of the selected solvent.

When $R_1$ represents hydrogen, it is preferable to protect the functional group with a protector group to facilitate the desired condensation reaction.

Regarding protective groups, it is possible to use the usual groups for protecting the hydroxyl group such as methoxyethoxymethyl (MEM), trimethylsilylethoxymethyl (SEM) or benzyl, employing well known techniques.

In the same manner, the other sensitive groups that may be present can be protected employing well known methods.

The epoxides of formula (II) are compounds that are known in the literature, or they can be prepared using methods that are analogous to the methods described in the literature.

The aminotetralins of formula (III) may be prepared according to procedures known in the literature, for example as described in EP-A-436435 or in EP-A-683236.

The compounds of formula (III) where $R_3$ and/or $R'_3$ are a —$(CH_2)_2COR_4$ group ($R_4$ as defined in formula (I), and their salts, are novel and constitute another aspect of the present invention; it being possible for these compounds to be prepared according to the procedure described in WO 01/94307 (Scheme 1).

The activity of the compounds of the present invention as regards beta-3 effect has been demonstrated through in vitro tests on the human colon using the method described by T. Croci et al., Br. J. Pharmacol., 1997, 122; 139P, by L. Manara et al., Gut, 2000, 47: 337–342 and in EP-A-436435. More particularly, it is observed that the compounds of formula (I) are much more active on the isolated colon than on the auricle and on the trachea.

These surprising properties of the compounds of formula (I) allow their use as drugs with a beta-3 agonist action to be envisaged.

Further, the compounds of formula (I) have low toxicity; in particular, their acute toxicity is compatible with their use as drugs in treating disorders in which compounds having an affinity for the beta-3 receptor, in particular beta-3 agonists, are applicable. Such disorders have been described in the literature. The compounds of formula (I) and their pharmaceutically acceptable salts can thus, for example, be indicated in the treatment of gastro-intestinal diseases such as inflammatory bowel diseases such as irritable bowel syndrome (IBD), as modulators for intestinal motricity, as lipolytics, as anti-obesity agents, as anti-diabetic agents, as psychotropic agents, as anti-glaucoma agents, as cicatrizing agents, as anti-depressants, as a uterine contraction inhibitor, as tocolytics to prevent or retard premature birth, or in the treatment and/or prophylaxis of dysmenorrhea. Further, the compounds of formula (I) can be used in treating certain disorders of the central nervous system, such as depression, for example, and certain problems with the urinary system such as urinary incontinence.

The use of the compounds of formula (I) above, and that of their pharmaceutically acceptable salts and solvates, for the preparation of the drugs designated above, constitutes a further aspect of the present invention.

For such a use, an effective quantity of a compound of formula (I) or one of its pharmaceutically acceptable salts and solvates is administered to mammals in need of such a treatment.

The above compounds of formula (I) and their pharmaceutically acceptable salts and solvates can be used in daily doses of 0.01 to 20 mg per kg of body weight of the mammal to be treated, preferably in daily doses of 0.1 to 10 mg/kg. In humans, the dose is preferably 0.5 mg to 1500 mg per day, in particular 2.5 to 500 mg depending on the age of the subject to be treated, the type of treatment—prophylactic or curative—and the severity of the disease. The compounds of formula (I) are generally administered in a dosage of 0.1 to 500 mg, preferably 0.5 to 100 mg of active principle, once to five times a day.

Said dosages are preferably formulated in pharmaceutical compositions in which the active principle is mixed with a pharmaceutical excipient.

In a further aspect, then, the present invention concerns pharmaceutical compositions comprising, as the active principle, a compound of formula (I) above or one of its pharmaceutically acceptable salts and solvates.

In the pharmaceutical compositions of the present invention for oral, sublingual, subcutaneous, intramuscular, intravenous, topical, transdermal or rectal administration, the active ingredients of formula (I) above, their pharmaceutically acceptable salts and solvates, can be administered to animals and humans in unitary administration forms mixed with conventional pharmaceutical supports to treat the diseases cited above. Suitable unitary administration forms comprise oral administration forms such as tablets, gelatin capsules, powders, granules and oral solutions or suspensions, sublingual and buccal administration forms, subcutaneous, intramuscular or intravenous administration forms, local administration forms and rectal administration forms.

When preparing a solid composition in the form of tablets, the principal active ingredient is mixed with a pharmaceutical vehicle such as gelatine, starch, lactose, magnesium stearate, talc, gum Arabic or the like. Tablets can be coated with sugar or with other suitable materials, or they can be treated so that they have a prolonged or slow effect and they continuously release a predetermined quantity of active principle.

A gelatin capsule preparation is obtained by mixing the active ingredient with a diluent and pouring the mixture obtained into soft or hard gelatin capsules.

A preparation in the form of a syrup or elixir can contain the active ingredient along with a sweetener, preferably calorie-free, methylparaben and propylparaben as antiseptics, and a suitable taste producing agent and colorant.

Water-dispersible powders or granules can contain the active ingredient mixed with dispersion agents or wetting agents, or suspension agents such as polyvinylpyrrolidone, and again with sweeteners or taste correcting agents.

For local administration, the active principle is mixed with an excipient for preparing creams or unguents or it is dissolved in a vehicle for intraocular administration, for example in the form of an eye lotion.

For rectal administration, suppositories are used that are prepared with binders that melt at the temperature of the rectum, for example cocoa butter or polyethylene glycols.

For parenteral administration, aqueous suspensions, saline solutions or sterile injectable solutions are used that contain pharmacologically compatible dispersion agents and/or wetting agents, for example propylene glycol or butylene glycol.

The active principle can also be formulated in the form of microcapsules, optionally with one or more supports or additives.

In a further aspect, the present invention concerns a method for treating diseases that are improved by a beta-3 agonist action, which comprises administering a compound of formula (I) or one of its pharmaceutically acceptable salts or solvates.

The compounds of formula (I), in particular compounds (I) labeled with an isotope, can also be used as laboratory tools in biochemical tests.

The compounds of formula (I) bind to the beta-3 adrenergic receptor. Thus, said compounds can be used in an ordinary binding test in which an organic tissue in which this receptor is particularly abundant is used, and the quantity of compound (I) displaced by a test compound is measured to determine the affinity of said compound towards binding sites for that particular receptor.

A further specific subject matter of the present invention is thus a reagent that can be used in biochemical tests, which comprises at least one suitably labeled compound of formula (I).

The following examples better illustrate the invention.

All the NMR spectra, unless otherwise stated, were recorded at 400 MHz.

In the description of the HPLC experiments: SP=Stationary Phase; MP=Mobile Phase; b.=buffer; f=flow rate; TR=Retention Time.

EXAMPLE 1

N-[2-Hydroxy-5-({(2S)-2-hydroxy-3-[(1,2,3,4-tetrahydro-2-naphthalenylmethyl)amino]propyl}oxy)phenyl]methane-sulfonamide (a). N-[2-Benzyloxy-5-({(2S)-2-hydroxy-3-[(1,2,3,4-tetrahydro-2-naphthalenylmethyl)amino]propyl}oxy)-phenyl]methanesulfonamide A mixture of 770 mg of 4-benzyloxy-3-(N-tert-butoxycarbonyl-N-methylsulfonylamino)-1-((2S)2,3-epoxypropoxy)benzene (1.71 mmol) and 300 mg (1.8 mmol) of 1,2,3,4-tetrahydronaphthalen-2-ylmethylamine, obtained as described in EP-A-436435, in 20 ml of absolute ethanol is heated under reflux for 16 hours. The mixture is cooled, 3 ml of an ethanol solution saturated with hydrochloric acid are added thereto and the medium is heated at 50° C. for 5 hours. The solvent is evaporated and the medium is taken up with a mixture of 50 ml of a saturated sodium bicarbonate solution and 50 ml of ethyl acetate. The organic phase is washed with a saturated aqueous NaCl solution. The organic phase is dried, filtered and the solvent is evaporated under reduced pressure. The crude product is purified by chromatography on a silica gel column, eluting with a methylene chloride/methanol=95/5 mixture. The title compound is obtained in the form of a glassy solid.

(b). N-[2-Hydroxy-5-({(2S)-2-hydroxy-3-[(1,2,3,4-tetrahydro-2-naphthalenylmethyl)amino]propyl}oxy)-phenyl]methanesulfonamide A solution of 400 mg of the product of example (1a) (0.8 mmol) in 25 ml of a mixture of ethanol and THF is stirred at ambient temperature and under a hydrogen atmosphere for 7 hours in the presence of 80 mg of 10% Pd/C. The catalyst is filtered, the solvent is evaporated under reduced pressure and the crude product is purified by chromatography on a silica gel column, eluting with a methylene chloride/methanol=9/1 mixture. The title compound is obtained.

Mass=MH$^+$421 NMR (DMSO+D20 313K); 200 MHz 1.27–1.59 (m; 1H); 1.80–2.26 (m; 2H); 2.34–2.57 (m; 1H); 2.67–2.88 (m; 2H); 2.93 (s; 3H); 2.97–3.13 (m; 3H); 3.13–3.31 (m; 1H); 3.83–3.98 (m; 2H); 6.67 (dd; 1H) Ja 8.8 Hz, Jb 2.9 Hz; 6.83 (d; 1H) J 8.8 Hz; 6.83 (d; 1H) J2.9 Hz; 7.06 (s; 4H).

EXAMPLE 2

N-{2-Hydroxy-5-[((2S)-2-hydroxy-3-{[(7-methoxy-1,2,3,4-tetrahydro-2-naphthalenyl)methyl]amino}propyl)oxy]-phenyl}methanesulfonamide (a). N-{2-Benzyloxy-5-[((2S)-2-hydroxy-3-{[(7-methoxy-1,2,3,4-tetrahydro-2-naphthalenyl)methyl]amino}propyl)-oxy]phenyl}methanesulfonamide By carrying out the procedure as in example (1a), with 7-methoxy-1,2,3,4-tetrahydronaphthalen-2-ylmethylamine obtained as described in EP-A-436435 the title compound is obtained in the form of a glassy solid.

(b). N-{2-Hydroxy-5-[((2S)-2-hydroxy-3-}[(7-methoxy-1,2,3,4-tetrahydro-2-naphthalenyl)methyl]amino}propyl)-oxy]phenyl}methanesulfonamide By carrying out the procedure as described in example (1b), with the product obtained in step (2a), the title compound is obtained.

Mass=MH+ 451 NMR (DMSO+TFA 313K); 200 MHz 1.24–1.52 (m; 1H); 1.91–2.29 (m; 2H); 2.41–2.48 (m; 1H); 2.58–3.29 (m; 7H); 2.92 (s; 3H); 3.66 (s; 3H); 3.74–3.98 (m; 2H); 4.07–4.30 (m; 1H); 6.54–6.73 (m; 3H); 6.73–6.89 (m; 2H); 6.89–7.02 (m; 1H).

EXAMPLE 3

N-{2-Hydroxy-5-[((2S)-2-hydroxy-3-{[(6-methoxy-1,2,3,4-tetrahydro-2-naphthalenyl)methyl]amino}propyl)oxy]-phenyl}methanesulfonamide (a). N-{2-Benzyloxy-5-[((2S)-2-hydroxy-3-{[(6-methoxy-1,2,3,4-tetrahydro-2-naphthalenyl)methyl]amino}propyl)-oxy]phenyl}methanesulfonamide By carrying out the procedure as in example (1a), with 6-methoxy-1,2,3,4-tetrahydronaphthalen-2-ylmethylamine obtained as described in EP-A-436435 the title compound is obtained in the form of a glassy solid.

(b). N-{2-Hydroxy-5-[((2S)-2-hydroxy-3-{[(6-methoxy-1,2,3,4-tetrahydro-2-naphthalenyl)methyl]amino}propyl)-oxy]phenyl}methanesulfonamide By carrying out the procedure as in example (1b), with the product obtained in step (3a), the title compound is obtained.
Mass=MH+ 451 NMR (DMSO 313K) 1.27–1.43 (m; 1H); 1.85–2.02 (m; 2H); 2.35 (dd; 1H) Ja 16 Hz, Jb 10 Hz; 2.62–2.84 (m; 6H); 2.88 (dd; 1H) Ja 12 Hz, Jb 4 Hz; 2.95 (s; 3H); 3.70 (s; 3H); 3.76–3.93 (m; 2H); 3.93–4.07 (m; 1H); 6.57–6.71 (m; 3H); 6.81 (d; 1H) J 9 Hz; 6.83 (d; 1H) J 3 Hz; 6.96 (d; 1H) J 8 Hz. HPLC=SP: SUPELCOSIL LC-ABZ 15×0.46 cm. MP: b. $KH_2PO_4$ 0.02M pH 3.5/$CH_3CN$/MeOH 80:18:2; f=1 ml/min; λ=205 nm; TR=9.05 min HPLC=SP: CHIRALCEL OD-H 25×0.46 cm. MP: hexane/ethanol 75:25; f=0.8 ml/min; λ=235 nm; $TR_1$=15.07 min (2S, 2R); $TR_2$=19.68 min (2S, 2S)

EXAMPLE 4

N-(2-Hydroxy-5-{[(2S)-2-hydroxy-3-({[(2R)-6-methoxy-1,2,3,4-tetrahydro-2-naphthalenyl]methyl}amino)-propyl)oxy}phenyl)methanesulfonamide (a). N-(2-Benzyloxy-5-{[(2S)-2-hydroxy-3-({[(2R)-6-methoxy-1,2,3,4-tetrahydro-2-naphthalenyl]methyl}amino)propyl]oxy}phenyl)methane-sulfonamide By carrying out the procedure as in example (1a), using (2R)-6-methoxy-1,2,3,4-tetrahydronaphthalen-2-ylmethylamine obtained as described in EP-A-683236, the title compound is obtained in the form of a glassy solid.

(b). N-(2-Hydroxy-5-{[(2S)-2-hydroxy-3-({[(2R)-6-methoxy-1,2,3,4-tetrahydro-2-naphthalenyl]methyl}amino)propyl]oxy}phenyl)methanesulfonamide By carrying out the procedure as in example (1b), with the product obtained in step (4a), the title compound is obtained.
Mass=MH+ 451 NMR (DMSO 313K) 1.18–1.38 (m; 1H); 1.70–1.98 (m; 2H); 2.26–2.36 (m; 1H); 2.53–2.58 (m; 2H); 2.60–2.82 (m; 5H); 2.94 (s; 3H); 3.63–3.73 (m; 3H); 3.73–3.82 (m; 1H); 3.82–3.91 (m; 1H); 6.63–6.69 (m; 3H); 6.72–6.84 (m; 2H); 6.94 (d; 1H) J 8 Hz. HPLC=SP: CHIRALCEL OD-H 25×0.46 cm. MP: hexane/ethanol 75:25; f=0.8 ml/min; λ=235 nm; $TR_1$=14.53 min (ee 84.2%).

EXAMPLE 5

N-{2-Hydroxy-5-[((2S)-2-hydroxy-3-{[(7-hydroxy-1,2,3,4-tetrahydro-2-naphthalenyl)methyl]amino}propyl)oxy]-phenyl}methanesulfonamide (a). N-{2-Benzyloxy-5-[((2S)-2-hydroxy-3-{[(7-hydroxy-1,2,3,4-tetrahydro-2-naphthalenyl)methyl]amino}propyl)-oxy]phenyl}methanesulfonamide By carrying out the procedure as in example (1a), with 7-hydroxy-1,2,3,4-tetrahydronaphthalen-2-ylmethylamine obtained as described in EP-A-436435, the title compound is obtained in the form of a glassy solid.

(b). N-{2-Hydroxy-5-[((2S)-2-hydroxy-3-{[(7-hydroxy-1,2,3,4-tetrahydro-2-naphthalenyl)methyl]amino}propyl)-oxy]phenyl}methanesulfonamide By carrying out the procedure as in example (1b), with the product of step (5a), but eluting with a $CH_2Cl_2$/$CH_3OH$/$NH_4OH$=9/1/0.1 mixture, the title compound is obtained.
Mass=MH+ 437 NMR (DMSO+D20 313K); 300 MHz 1.18–1.44 (m; 1H); 1.64–2.03 (m; 2H); 2.20–2.41 (m; 1H); 2.54–2.85 (m; 6H); 2.93 (s; 3H); 3.72–4.04 (m; 3H); 5.46–5.90 (m; 1H); 6.23–6.56 (m; 2H); 6.56–6.72 (m; 1H); 6.72–7.01 (m; 3H). HPLC=SP: SUPELCOSIL LC-ABZ 15×0.46 cm. MP: b. $K_2HPO_4$ 0.02M pH 7.0/MeOH 7:3; f=1 ml/min; λ=295 nm; TR=35.2 min.

EXAMPLES 6–14

By carrying out the procedure described in example 1, but using the appropriate epoxides and aminomethyltetralins, the compounds presented in the following table are obtained:

TABLE

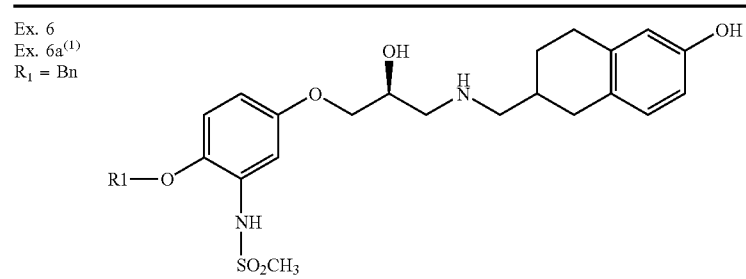

Ex. 6
Ex. 6a(1)
$R_1$ = Bn

TABLE-continued

| Ex. 6b | Mass = MH⁺ 437 |
|---|---|
| $R_1$ = H | NMR (DMSO + D2O 313K) |
| | 1.16–1.42 (m; 1H); 1.61–1.98 (m; 2H); 2.11–2.34 (m; 1H); 2.41–2.54 (m; 2H); |
| | 2.54–2.77 (m; 5H); 2.90 (s; 3H); 3.72–3.80 (m; 1H); 3.80–3.92 (m; 2H); 6.35– |
| | 6.54 (m; 2H): 6.56 (dd; 1H) Ja 9Hz, Jb 3Hz; 6.76 (d; 1H) J 9Hz; 6.78–6.91 (m; 2H). |
| | HPLC = SP: SUPELCOSIL LC-ABZ 15 × 0.46 cm. MP: b. $K_2HPO_4$ 0.01M |
| | pH 7.0/MeOH 65:35; f = 1 ml/min; λ = 225 nm; TR = 13.2 min |

Ex. 7
Ex. 7a[(1)]
$R_1$ = Bn

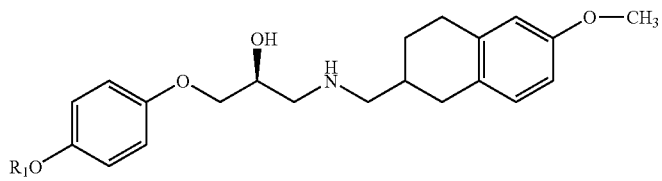

| Ex. 7b | Mass = MH⁺ 358 |
|---|---|
| $R_1$ = H | NMR (DMSO + D2O 313K) |
| | 1.17–1.39 (m; 1H); 1.67–1.96 (m; 2H); 2.28 (dd; 1H); Ja 16Hz, Jb 11Hz; 2.52– |
| | 2.60 (m; 1H); 2.60–2.81 (m; 4H); 3.67 (s; 3H); 3.72–3.91 (m; 3H); 6.55–6.70 |
| | (m; 4H); 6.70–6.79 (m; 2H); 6.93 (d, 1H) J 8Hz. |
| | HPLC = SP: SUPELCOSIL LC-ABZ + Plus 15 × 0.46 cm. MP: b. $K_2HPO_4$ |
| | 0.02M pH 7.0/MeOH 1:1; f = 1 ml/min; λ = 225 nm; TR = 9.07 min. |

Ex. 8
Ex. 8a[(1)]
$R_1$ = Bn

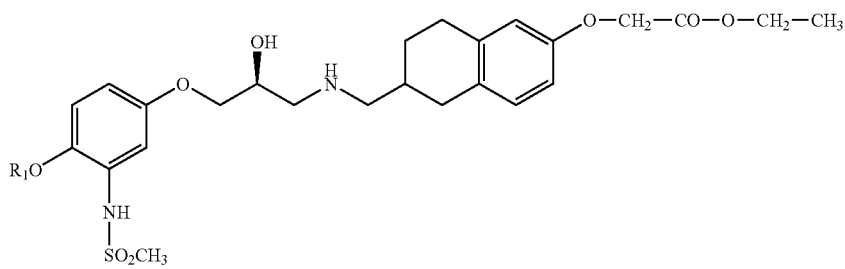

| Ex. 8b | Mass = MH⁺ 523 |
|---|---|
| $R_1$ = H | NMR (DMSO + D2O 313K) |
| | 1.21 (t; 3H); J 7Hz; 1.24–1.38 (m; 1H); 1.73–2.01 (m; 2H); 2.20–2.39 (m; 1H); |
| | 2.54–2.83 (m; 7H); 2.94 (s; 3H); 3.73–3.95 (m; 3H); 4.16 (q; 2H); J 7Hz; 4.69 |
| | (s; 2H): 6.54–6.69 (m; 3H); 6.79 (d, 1H) J 9Hz; 6.81 (d; 1H) J 3Hz; 6.96 (d; 1H) J 8Hz. |
| | HPLC = SP: SUPELCOSIL LC-ABZ + Plus 15 × 0.46 cm. MP: b. $K_2HPO_4$ |
| | 0.02M pH 7.0/MeOH 1:1; f = 1 ml/min; λ = 225 nm; TR = 6.3 min. |

Ex. 9
Ex. 9a[(1)]
$R_1$ = Bn

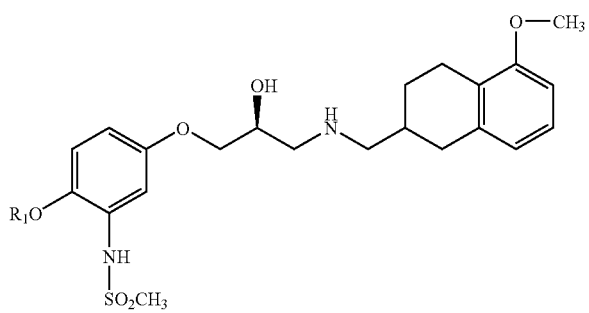

| Ex. 9b | Mass = MH⁺ 451 |
|---|---|
| $R_1$ = H | NMR (DMSO + D2O 313K) |
| | 1.17–1.40 (m; 1H); 1.65–1.86 (m; 1H); 1.86–2.47 (m; 1H); 2.52–2.85 (m; 6H); |
| | 2.92 (s; 3H); 3.73 (s; 3H); 3.73–4.07 (m; 3H); 6.46–6.88 (m; 5H); 6.88–7.16 (m; 1H). |
| | HPLC = SP: SUPELCOSIL LC-ABZ + Plus 15 × 0.46 cm. MP: b. $K_2HPO_4$ |
| | 0.02M pH 7.0/$CH_3CN$ 3:7; f = 1 ml/min; λ = 225 nm; TR = 1.8 min. |

TABLE-continued

Ex. 10
Ex. 10a(1)
R₁ = Bn

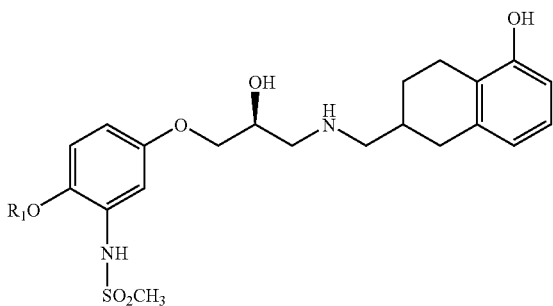

Ex. 10b   Mass = MH⁺ 437
R₁ = H    NMR (DMSO + D2O 313K)
          1.18–1.47 (m; 1H); 1.65–2.07 (m; 2H); 2.20–2.45 (m; 2H); 2.53–2.85 (m; 6H);
          2.90 (s; 3H); 3.74–4.00 (m; 3H); 6.33–6.95 (m; 6H).

Ex. 11
Ex. 11a(2)
R₁ = Bn

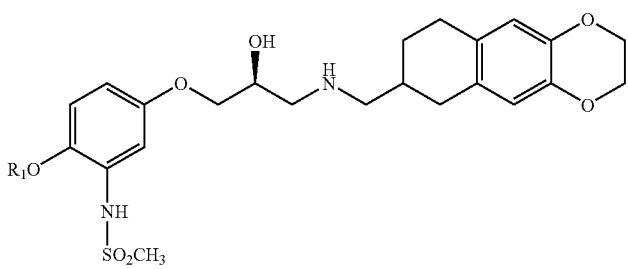

Ex. 11b   Mass = MH⁺ 479
R₁ = H    NMR (DMSO 313K)
          1.17–1.34 (m; 1H); 1.68–1.97 (m; 2H); 2.26 (dd; 1H); Ja 16Hz, Jb 10Hz;
          2.51–2.78 (m; 7H); 2.94 (s; 3H); 3.70–3.94 (m; 3H); 4.16 (bs; 4H); 6.51 (bs;
          2H): 6.62 (dd; 1H) Ja 9Hz, Jb 3Hz; 6.78 (d; 1H) J 8Hz; 6.81 (d; 1H) J 3Hz.
          HPLC = SP: SUPELCOSIL LC-ABZ + Plus 15 × 0.46 cm. MP: b. K₂HPO₄
          0.02M pH 7.0/MeOH 1:1; f = 1 ml/min; λ = 225 nm; TR = 5.56 min.

Ex. 12
Ex. 12a(3)
R₁ = Bn

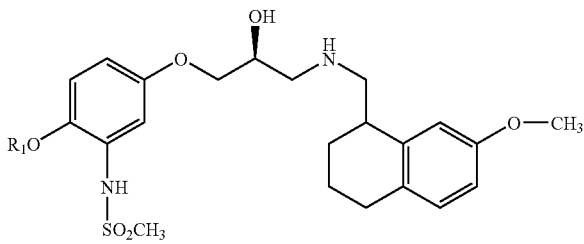

Ex. 12b   Mass = MH⁺ 451
R₁ = H    NMR (DMSO 313K)
          1.52–1.89 (m; 4H); 2.53–2.97 (m; 7H); 2.94 (s; 3H); 3.69 (s; 3H); 3.74–3.82
          (m, 1H); 3.82–3.94 (m; 2H); 6.62 (dd; 1H); Ja 9Hz, Jb 3Hz; 6.63 (dd; 1H); Ja
          8Hz, Jb 3Hz; 6.73 (m; 2H); 6.81 (dd; 1H) J 3Hz; 6.94 (dd; 1H) J 8Hz.
          HPLC = SP: XTerra ™ RP18 15 × 0.3 cm. MP: TEA-CH₃COOH pH
          10.0/CH₃CN 7:3; f = 0.5 ml/min; λ = 225 nm; TR = 7.14 min.

Ex. 13
Ex. 13a(4)
R₁ = Bn

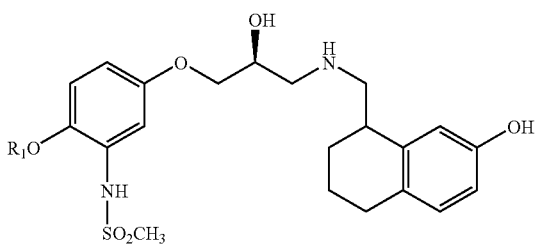

Ex. 13b   Mass = MH⁺ 437
R₁ = H    NMR (DMSO 313K)
          1.45–1.89 (m; 4H); 2.53–2.82 (m; 7H); 2.94 (s; 3H); 3.17 (s; 1H); 3.72–3.82
          (m; 1H); 3.82–3.93 (m; 2H); 6.49 (dd; 1H); Ja 8Hz, Jb 2Hz; 6.56–6.67 (m;
          2H): 6.78 (d; 1H) J 9Hz, 6.80–6.87 (m; 2H).

TABLE-continued

HPLC = SP: SUPELCOSIL LC-ABZ + Plus 15 × 0.46 cm. MP: b. $K_2HPO_4$
0.02M pH 7.0/$CH_3CN$ 3:7; f = 1 ml/min; λ = 225 nm; TR = 1.97 min.

Ex. 14
Ex. 14a[(5)]
$R_1$ = Bn

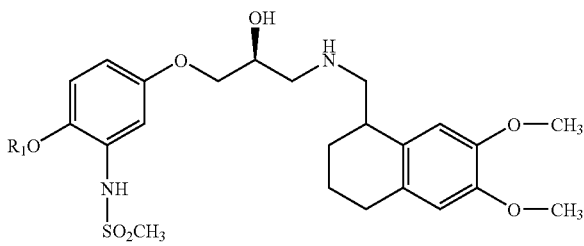

| Ex. 14b | Mass = $MH^+$ 481 |
| --- | --- |
| $R_1$ = H | NMR (DMSO 313K) |
| | 1.50–1.88 (m; 4H); 2.54–2.84 (m; 7H); 2.93 (s; 3H); 3.69 (bs; 6H); 3.74–3.94 (m; 3H); 6.59 (s; 1H); 6.52–6.65 (m; 1H); 6.77 (d; 1H); J 9Hz; 6.79 (s; 1H); 6.81 (d; 1H); J 3Hz. |
| | HPLC = SP: SUPELCOSIL LC-ABZ + Plus 15 × 0.46 cm. MP: b. $K_2HPO_4$ 0.02M pH 7.0/$CH_3CN$ 7:3; f = 1 ml/min; λ = 225 nm; TR = 4.82 min. |

Notes:
Bn = benzyl
[(1)] = aminomethyltetralin described in EP-A-436435.
[(2)] = aminomethyltetralin prepared according to the procedure described in EP-A-436435 from 2,3,8,9-tetrahydronaphtho[2,3-b]-1,4-dioxin-6-one described in Biorg. Med. Chem. Lett. 6 (10) : 1071, 1966.
[(3)] = aminomethyltetralin described in J. Med. Chem. 18 (12) : 1266, 1975.
[(4)] = aminomethyltetralin obtained by demethylation of the aminomethyltetralin [(3)] above.
[(5)] = aminomethyltetralin described in J. Med. Chem. 26 (6) : 813, 1983.

The invention claimed is:

1. A compound of formula (I):

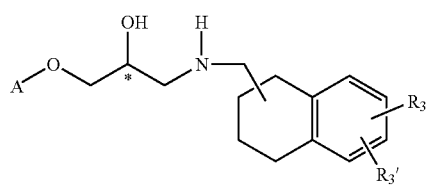

in which:

A is a group of formula (a) or (b)

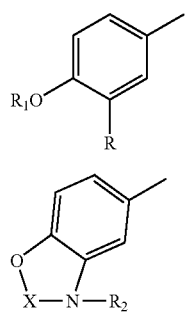

where

R represents a hydrogen or halogen atom, an $-S(O)_2(C_1-C_4)$alk group where z is 0, 1 or 2, an $-NHSO_2(C_1-C_4)$alk, $-SO_2NH(C_1-C_4)$alk, $-NHSO_2-(C_1-C_4)$alk-phenyl or $-NHSO_2$-phenyl group, it being possible for said phenyl to carry a halogen atom, a $(C_1-C_4)$alk group or a $(C_1-C_6)$alkoxy group;

$R_1$ represents a hydrogen atom or a $-(C_1-C_4)$alk, $-CO(C_1-C_4)$alk, $-(C_1-C_4)$alk-phenyl or $-CO$-phenyl-group, it being possible for said phenyl to carry a halogen atom or a $-(C_1-C_4)$alk or $(C_1-C_6)$alkoxy group;

$R_2$ is a hydrogen atom, an $-SO_2(C_1-C_4)$alk, $-SO_2-(C_1-C_4)$alk-phenyl, $-SO_2$-phenyl, or a $-(C_1-C_4)$alk group;

X completes a saturated or unsaturated 5- to 8-atom ring which can carry one or two $-(C_1-C_4)$alk groups and/or one or two carbonyl groups;

$R_3$ and $R'_3$ each represent independently a hydrogen or halogen atom, a $-(C_1-C_6)$alk, hydroxyl, $-CN$, $-(C_1-C_6)$alkoxy, $-COR_4$ or $-Y-CR_8R_9-COR_4$ group;

Y represents O or $CH_2$;

$R_4$ represents a hydroxyl, $(C_1-C_6)$alkoxy or $-NR_5R_6$ group;

$R_5$ and $R_6$ represent independently a hydrogen atom; a $-(C_1-C_4)$alk, aryl or heteroaryl group optionally substituted with an $R_7$ group, an aralkyl or heteroaralkyl group optionally substituted with an $R_7$ group;

or else $R_5$ and $R_6$, with the nitrogen atom carrying them, form a saturated or unsaturated 5- to 7-atom ring optionally substituted with an $R_7$ group;

$R_7$ represents a hydrogen or halogen atom, a hydroxyl, $-(C_1-C_4)$alk, $-(C_1-C_6)$alkoxy, $-NH(C_1-C_4)$alk, $-N(C_1-C_4)alk_2$, $-COO(C_1-C_4)$alk, aralkyl or heteroaralkyl group; and $R_8$ and $R_9$ represent independently a hydrogen atom or a $-(C_1-C_4)$alk group; or a salt thereof.

2. A compound according to claim 1 wherein the configuration of the carbon of the propanolamine carrying the OH group is (S).

3. A compound according to claim 1 wherein A is a group of formula (a).

4. A compound according to claim 3 wherein R is an $-NHSO_2(C_1-C_4)$alk group.

5. A compound according to claim 4 wherein $R_1$ is a hydrogen atom.

6. A compound according to claim 1 wherein $R_3$ and/or $R'_3$ are a hydrogen atom, a hydroxyl, —($C_1$–$C_6$)alkoxy or —Y—$CR_8R_9$—$COOCH_2$—$CH_3$ group.

7. A compound selected from the group consisting of:
N-[2-Benzyloxy-5-({(2S)-2-hydroxy-3-[(1,2,3,4-tetrahydro-2-naphthalenylmethyl)amino]-propyl}oxy)phenyl]methane sulfonamide;
N-[2-Hydroxy-5-({(2S)-2-hydroxy-3-[(1,2,3,4-tetrahydro-2-naphthalenylmethyl)amino]propyl}oxy)phenyl]methanesulfonamide;
N-{2-Benzyloxy-5-[((2S)-2-hydroxy-3-{[(7-methoxy-1,2,3,4-tetrahydro-2-naphthalenyl)methyl]amino}propyl)oxy]phenyl}methanesulfonamide;
N-{2-Hydroxy-5-[((2S)-2-hydroxy-3-{[(7-methoxy-1,2,3,4-tetrahydro-2-naphthalenyl)methyl]amino}propyl)oxy]phenyl}methanesulfonamide;
N-{2-Benzyloxy-5-[((2S)-2-hydroxy-3-{[(6-methoxy-1,2,3,4-tetrahydro-2-naphthalenyl)methyl]amino}propyl)oxy]phenyl}methanesulfonamide;
N-{2-Hydroxy-5-[((2S)-2-hydroxy-3-{[(6-methoxy-1,2,3,4-tetrahydro-2-naphthalenyl)methyl]amino}propyl)oxy]phenyl}methane sulfonamide;
N-(2-Benzyloxy-5-{[(2S)-2-hydroxy-3-({[(2R)-6-methoxy-1,2,3,4-tetrahydro-2-naphthalenyl]methyl}amino)propyl]oxy}phenyl)methanesulfonamide;
N-(2-Hydroxy-5-{[(2S)-2-hydroxy-3-({[(2R)-6-methoxy-1,2,3,4-tetrahydro-2-naphthalenyl]methyl}amino)propyl]oxy}phenyl}methanesulfonamide;
N-{2-Benzyloxy-5-[((2S)-2-hydroxy-3-{[(7-hydroxy-1,2,3,4-tetrahydro-2-naphthalenyl)methyl]amino}propyl)oxy]phenyl}methanesulfonamide;
N-{2-Hydroxy-5-[((2S)-2-hydroxy-3-{[(7-hydroxy-1,2,3,4-tetrahydro-2-naphthalenyl)methyl]amino}propyl)oxy]phenyl}methanesulfonamide;
N-{2-Benzyloxy-5-[((2S)-2-hydroxy-3-{[(6-hydroxy-1,2,3,4-tetrahydro-2-naphthalenyl)methyl]amino}propyl)oxy]phenyl}methanesulfonamide;
N-{2-Hydroxy-5-[((2S)-2-hydroxy-3-{[(6-hydroxy-1,2,3,4-tetrahydro-2-naphthalenyl)-methyl]amino}propyl)oxy]phenyl}methane sulfonamide;
(2S)-1-[4-Benzyloxyphenoxy]-3-{[(6-methoxy-1,2,3,4-tetrahydro-2-naphthalenyl)methyl]amino}-2-propanol;
4-[((2S)-2-Hydroxy-3-{[(6-methoxy-1,2,3,4-tetrahydro-2-naphthalenyl)methyl]amino}propyl)oxy]phenol;
Ethyl [(6-{[((2S)-3-{4-benzyloxy-3-[(methylsulfonyl)amino]phenoxy}-2-hydroxypropyl)-amino]methyl}-5,6,7,8-tetrahydro-2-naphthalenyl)oxy]acetate;
Ethyl [(6-{[((2S)-2-hydroxy-3-{4-hydroxy-3-[(methylsulfonyl)amino]-phenoxy}propyl)amino]methyl}-5,6,7,8-tetrahydro-2-naphthalenyl)oxy]acetate;
N-{2-Benzyloxy-5-[((2S)-2-hydroxy-3-{[(5-methoxy-1,2,3,4-tetrahydro-2-naphthalenyl)-methyl]amino}propyl)oxy]phenyl}methanesulfonamide;
N-{2-Hydroxy-5-[((2S)-2-hydroxy-3-{[(5-methoxy-1,2,3,4-tetrahydro-2-naphthalenyl)-methyl]amino}propyl)oxy]phenyl}methanesulfonamide;
N-{2-Benzyloxy-5-[((2S)-2-hydroxy-3-{[(5-hydroxy-1,2,3,4-tetrahydro-2-naphthalenyl)-methyl]amino}propyl)oxy]phenyl}methanesulfonamide;
N-{2-Hydroxy-5-[((2S)-2-hydroxy-3-{[(5-hydroxy-1,2,3,4-tetrahydro-2-naphthalenyl)-methyl]amino}propyl)oxy]phenyl}methanesulfonamide;
N-[2-Benzyloxy-5-({(2S)-3-[(2,3,6,7,8,9-hexahydronaphtho[2,3-b][1,4]dioxin-7-ylmethyl)amino]-2-hydroxypropyl}oxy)phenyl]methanesulfonamide;
N-[5-({(2S)-3-[(2,3,6,7,8,9-Hexahydronaphtho[2,3-b][1,4]dioxin-7-ylmethyl)amino]-2-hydroxypropyl}oxy)-2-hydroxyphenyl]methanesulfonamide;
N-{2-Benzyloxy-5-[((2S)-2-hydroxy-3-{[(7-methoxy-1,2,3,4-tetrahydro-1-naphthalenyl)-methyl]amino}propyl)oxy]phenyl}methanesulfonamide;
N-{2-Hydroxy-5-[((2S)-2-hydroxy-3-{[(7-methoxy-1,2,3,4-tetrahydro-1-naphthalenyl)-methyl]amino}propyl)oxy]phenyl}methanesulfonamide;
N-{2-Benzyloxy-5-[((2S)-2-hydroxy-3-{[(7-hydroxy-1,2,3,4-tetrahydro-1-naphthalenyl)-methyl]amino}propyl)oxy]phenyl}methanesulfonamide;
N-{2-Hydroxy-5-[((2S)-2-hydroxy-3-{[(7-hydroxy-1,2,3,4-tetrahydro-1-naphthalenyl)-methyl]amino}propyl)oxy]phenyl}methanesulfonamide;
N-{2-Benzyloxy-5-[((2S)-3-{[(6,7-dimethoxy-1,2,3,4-tetrahydro-1-naphthalenyl)methyl]-amino}-2-hydroxypropyl)oxy]phenyl}methanesulfonamide; and
N-{5-[((2S)-3-{[(6,7-Dimethoxy-1,2,3,4-tetrahydro-1-naphthalenyl)methyl]amino}-2-hydroxypropyl)oxy]-2-hydroxyphenyl}methanesulfonamide;
or a salt thereof.

8. A process for preparing a compound according to claim 1 which comprises reacting a compound of formula (II)

with an amine of formula (III)

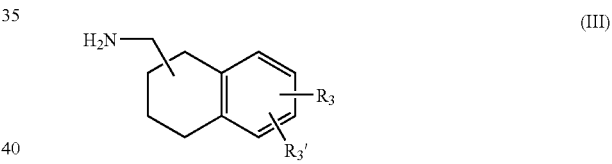

in the form of a nonsalified base, where A, $R_3$ and $R'_3$ are as defined in claim 1, and optionally converting the compound thus obtained into one of its salts.

9. A compound according to claim 2 wherein A is a group of formula (a).

10. A compound according to claim 9 wherein R is an —$NHSO_2(C_1$–$C_4)$alk group.

11. A compound according to claim 10 wherein $R_1$ is a hydrogen atom.

12. A compound according to claim 2 wherein $R_3$ and/or $R'_3$ are a hydrogen atom, a hydroxyl, —($C_1$–$C_6$)alkoxy or —Y—$CR_8R_9$—$COOCH_2$—$CH_3$ group.

13. A compound according to claim 3 wherein $R_3$ and/or $R'_3$ are a hydrogen atom, a hydroxyl, —($C_1$–$C_6$)alkoxy or —Y—$CR_8R_9$—$COOCH_2$—$CH_3$ group.

14. A compound according to claim 4 wherein $R_3$ and/or $R'_3$ are a hydrogen atom, a hydroxyl, —($C_1$–$C_6$)alkoxy or —Y—$CR_8R_9$—$COOCH_2$—$CH_3$ group.

15. A compound according to claim 5 wherein $R_3$ and/or $R'_3$ are a hydrogen atom, a hydroxyl, —($C_1$–$C_6$)alkoxy or —Y—$CR_8R_9$—$COOCH_2$—$CH_3$ group.

16. A pharmaceutical composition comprising a compound according to claim 1 together with a pharmaceutically acceptable excipient.

17. A pharmaceutical composition comprising a compound according to claim 7 together with a pharmaceutically acceptable excipient.

18. A pharmaceutical composition comprising a compound according to claim 11 together with a pharmaceutically acceptable excipient.

19. A pharmaceutical composition comprising a compound according to claim 15 together with a pharmaceutically acceptable excipient.

20. A method for the treatment of obesity which comprises administering to a patient in need of such treatment a therapeutically effective amount of a compound according to claim 1.

21. A method for the treatment of obesity which comprises administering to a patient in need of such treatment a therapeutically effective amount of a compound according to claim 7.

22. A method for the treatment of obesity which comprises administering to a patient in need of such treatment a therapeutically effective amount of a compound according to claim 11.

23. A method for the treatment of obesity which comprises administering to a patient in need of such treatment a therapeutically effective amount of a compound according to claim 15.

* * * * *